(12) United States Patent
Horng et al.

(10) Patent No.: US 6,894,580 B2
(45) Date of Patent: May 17, 2005

(54) FILTER TUNER SYSTEM AND METHOD

(75) Inventors: Brian Horng, Irvine, CA (US); Benedict A. Itri, Huntington Beach, CA (US); Devin Ng, Mission Viejo, CA (US); John Ross, Aberdeen, NJ (US); James J. Zhao, Tustin, CA (US)

(73) Assignee: GlobespanVirata, Inc, Red Bank, NJ (US)

( * ) Notice: Subject to any disclaimer, the term of this patent is extended or adjusted under 35 U.S.C. 154(b) by 224 days.

(21) Appl. No.: 09/971,484

(22) Filed: Oct. 5, 2001

(65) Prior Publication Data

US 2002/0067220 A1 Jun. 6, 2002

Related U.S. Application Data

(60) Provisional application No. 60/238,276, filed on Oct. 5, 2000.

(51) Int. Cl.[7] .................................................. H04B 3/04
(52) U.S. Cl. ..................................... 333/17.1; 333/174
(58) Field of Search ............................... 333/17.1, 174; 455/226.1, 266, 340

(56) References Cited

U.S. PATENT DOCUMENTS

| | | | | |
|---|---|---|---|---|
| 5,281,931 A | * | 1/1994 | Bailey et al. | 333/17.1 |
| 5,995,817 A | * | 11/1999 | Lubbe et al. | 455/266 |
| 6,219,392 B1 | * | 4/2001 | Abe | 375/350 |
| 6,492,922 B1 | * | 12/2002 | New | 341/120 |
| 6,597,238 B1 | * | 7/2003 | Matsumoto et al. | 329/300 |

* cited by examiner

*Primary Examiner*—Benny Lee
*Assistant Examiner*—Kimberly Glenn
(74) *Attorney, Agent, or Firm*—Thomas, Kayden, Horstemeyer & Risley (57) ABSTRACT

A system and method for a filter tuner is presented. The system comprises a sequential logic, a register, a comparator, a first and second counter, a synchronizing logic, a first and second oscillator, a control logic, and a first and second combinational logic. The method comprises the steps of executing a calibration cycle of a filter tuner, executing a measurement cycle of the filter tuner, and tuning a filter with the filter tuner dependent on a determined cutoff frequency variation.

22 Claims, 8 Drawing Sheets

FILTER TUNER SYSTEM AND METHOD

CROSS-REFERENCE TO RELATED APPLICATION

The present application claims the benefit of U.S. provisional patent application, issued Ser. No. 60/238,276, and filed Oct. 5, 2000, which is hereby incorporated by reference in its entirety.

FIELD OF THE INVENTION

The present invention generally relates to communications systems wherein signal information is processed in analog forms. More specifically, the invention relates to systems and methods for tuning resistance-capacitance ("RC") continuous-time filters.

BACKGROUND OF THE INVENTION

RC continuous-time filters are utilized in various applications, such as in communications systems. As with other types of filters, RC continuous-time filters may be designed to selectively filter out the parts of a signal that have frequencies above or below a desired cutoff frequency. Typically, RC continuous-time filters are utilized in applications where the signals are expected to remain continuous in time and have analog levels. Since continuous-time filters can typically be utilized without the need for signal sampling, continuous-time filters provide a significant operating-speed advantage over the switched-capacitor filter counterparts.

Figure 1:
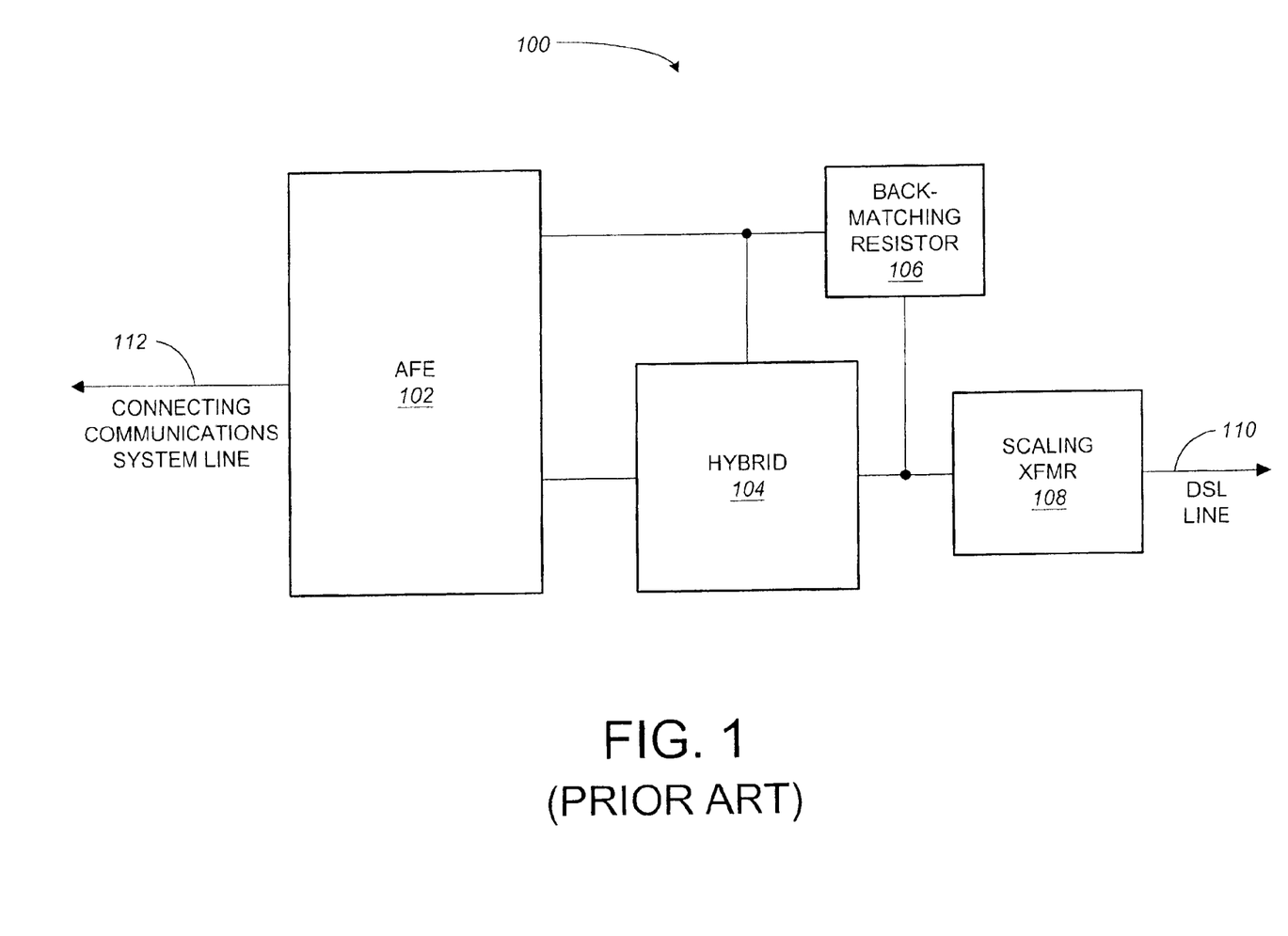
FIG. 1 is a block diagram of a typical DSL communications system as is known in the art.

One example of a popular application in which RC continuous-time filters are utilized is digital subscriber line ("DSL") communications systems. DSL communications systems have been introduced and implemented by communications systems providers in recent years to provide customers with a wide variety of interactive multi-media communications signals over existing plain old telephone system ("POTS") communications lines. As shown in FIG. 1, and known in the art, a typical DSL communications system 100 includes several basic components. It is noted that FIG. 1 merely presents a simplified representation of a typical DSL communications system that is sufficient for the purpose of this discussion.

As shown in FIG. 1, a typical DSL communications system 100 includes an analog front end ("AFE") 102, a hybrid 104, a back-matching resistor 106, a scaling transformer 108, one or more DSL lines 110, and one or more connecting communications system lines 112. An AFE 102 is a primary interface component between a DSL communications system and other types of communications systems, such as T-carrier (e.g., T1, T3) or optical-carrier (e.g., OC-1, OC-48) communications systems. Although not shown in FIG. 1, a complete DSL communications system typically includes two or more of the DSL systems 100 interconnected via one or more DSL lines 110.

Within an AFE of a DSL communications system, such as that depicted in FIG. 1, one or more RC continuous-time filters may be utilized. Typically, the components of a DSL system, with the exception of some portions of the communications lines, are contained in a common location. As a result of this practice, DSL system components, including RC continuous-time filters integrated within an AFE, may be subject to temperature variations affected by ambient temperature variations as well as by variations in operating conditions (e.g., signal strengths or operating durations). For example, in typical applications of DSL communications systems, operating temperatures of system components may vary from −40° C. to 125° C. due to ambient temperature and/or operating condition variations. It is noted that the preceding discussion, with respect to DSL communications systems, merely presents one example of the utilization of RC continuous-time filters, and there are many other applications in which RC continuous-time filters are or may be utilized and in which temperature variation may be a concern.

Although RC continuous-time filters offer an operating-speed advantage, as discussed above, these filters typically require some means of tuning in order to set and maintain a desired cutoff frequency. A major reason that tuning of RC continuous-time filters is necessary is because the cutoff frequency of the filter is dependent on the values of the resistance and capacitance elements of the filter, and these values will typically vary due to temperature variations. For example, in a filter built with "High-resitivity Poly0" resistors and "Interpoly" capacitors (note, these component types are known in the art and have certain temperature variation characteristics), the variation in cutoff frequency may vary by as much as 0.15%/° C. In contrast, an acceptable range of cutoff frequency variation, depending on the application, is typically less than 0.04%/° C. It is noted that in an RC continuous-time filter that is built with High-resitivity Poly0 resistors and Interpoly capacitors, the temperature variation of the RC component of the filter, and thus the cutoff frequency of the filter, is typically dominated by the temperature variation of the resistors which can be as large as 0.15%/° C.

Therefore, there is a need for a system and method for a filter tuner for tuning RC continuous-time filters in order to set and maintain cutoff frequencies within acceptable tolerances with regard to temperature variations.

SUMMARY OF THE INVENTION

Certain objects, advantages, and novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve various objects and advantages, the present invention is directed to a novel system and method for a filter tuner. In accordance with some embodiments of the present invention, a system for filter tuning is provided that includes a sequential logic, a register, a comparator, a first and second counter, a synchronizing logic, a first and second oscillator, a control logic, and a first and second combinational logic.

In accordance with other embodiments of the present invention, a method for a filter tuner is provided that includes the steps of executing a calibration cycle of a filter tuner, executing a measurement cycle of the filter tuner, and tuning the filter with the filter tuner dependent on a determined cutoff frequency variation.

The embodiments of the present invention provide at least the advantage of a system and method for a filter tuner that tunes RC continuous-time filters in order to set and maintain cutoff frequencies within acceptable tolerances with regard to temperature variations.

Other objects, features, and advantages of the present invention will become apparent to one skilled in the art upon examination of the following drawings and detailed description. It is intended that all such additional objects, features, and advantages be included herein within the scope of the present invention, as defined by the claims.

BRIEF DESCRIPTION OF THE DRAWINGS

The present invention will be more fully understood from the detailed description given below and from the accompanying drawings of a preferred embodiment of the invention, which however, should not be taken to limit the invention to the specific embodiments enumerated, but are for explanation and for better understanding only. Furthermore, the drawings are not necessarily to scale, emphasis instead being placed upon clearly illustrating the principles of the invention. Finally, like reference numerals in the figures designate corresponding parts throughout the several drawings.

DETAILED DESCRIPTION OF THE EMBODIMENTS

Having summarized the invention above, reference is now made in detail to the description of the invention as illustrated in the drawings. While the invention will be described in connection with these drawings, there is no intent to limit it to the embodiment or embodiments disclosed therein. On the contrary, the intent is to cover all alternatives, modifications, and equivalents included within the spirit and scope of the invention as defined by the appended claims. Indeed, the present invention is believed to be applicable to a variety of systems, devices, and technologies.

Figure 2A:
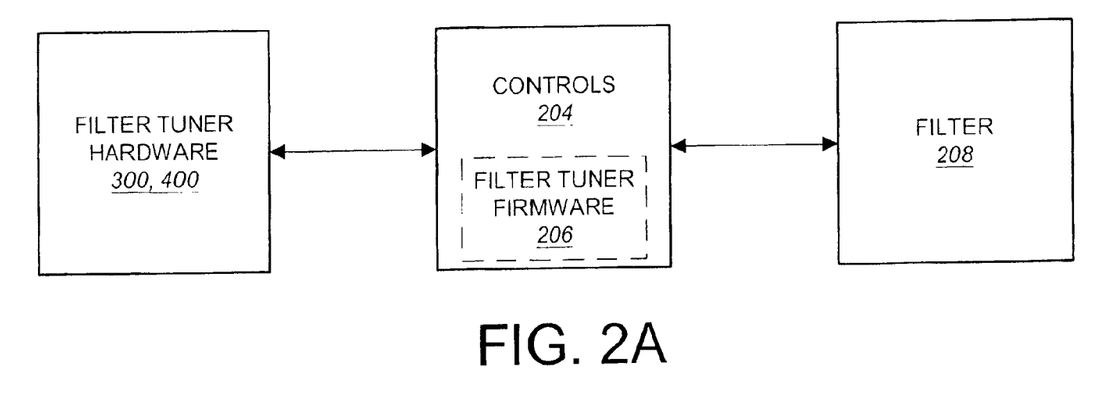
FIG. 2A is a block diagram depicting the utilization of an embodiment of the present invention as it may be utilized in a filter tuning application.

Turning now to the drawings, wherein like referenced numerals designate corresponding parts throughout the drawings, FIG. 2A shows a block diagram depicting the utilization of an embodiment of the present invention as it may be utilized in a filter tuning application. In such a filter tuning application, a filter tuner hardware 300, 400 in accordance with an embodiment of the present invention, may be in electrical communications with controls 204. Further, controls 204 may be in electrical communications with a filter 208. The filter tuner hardware 300, 400 is described in further detail below, but generally, the hardware 300, 400 may operate to monitor the accuracy of the filter 208 and cause adjustments to the filter 208 to set or maintain its cutoff frequency accuracy. Controls 204 may include one or more processors, digital signal processors ("DSPs"), or other circuitry elements that may control the adjustment or accuracy of the filter 208 in response to signals communicated with the filter tuner hardware 300. The filter 208 may be one or more of a variation of RC continuous-time filters such as, for example, a variation of a low-pass, high-pass, or band-pass filter.

As shown in FIG. 2A, controls 204 may include filter tuner firmware 206, in accordance with an embodiment of the present invention. The filter tuner firmware 206 may include various forms of logic, software, executable code, or other forms within the scope of the embodiments of the present invention, as will be apparent to one skilled in the art. The filter tuner firmware 206 may reside in a memory (not shown) such as a read-only memory ("ROM") or programmable read-only memory ("PROM") located with the controls 206 (as depicted) or at some other location (not depicted) with the components of the filter tuning application. The firmware 206 is described in further detail below, but generally, the firmware 206 may communicate control or data signals with the filter tuner hardware 300, 400. The firmware 206 may also communicate control or data signals with controls 204.

Figure 2B:
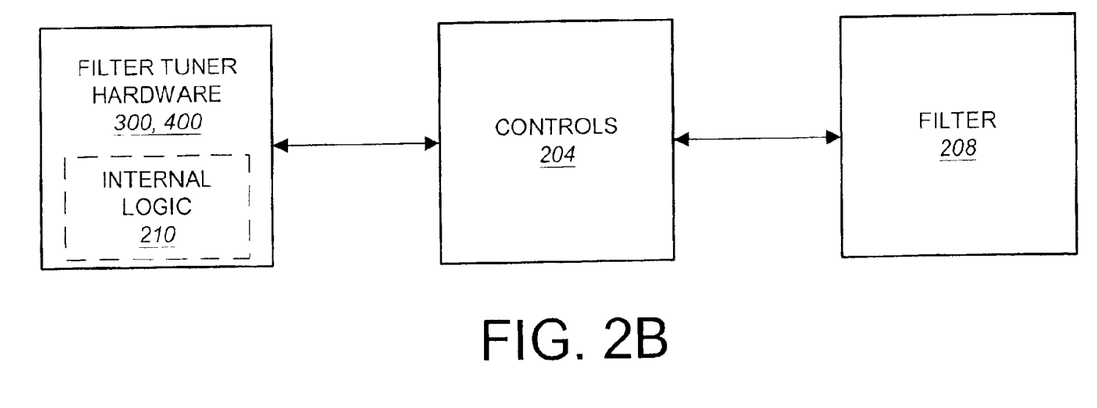
FIG. 2B is a block diagram depicting the utilization of another embodiment of the present invention as it may be utilized in a filter tuning application.

FIG. 2B shows a block diagram depicting the utilization of another embodiment of the present invention as it may be utilized in a filter tuning application. Similar to the previous description, in such a filter tuning application, a filter tuner hardware 300, 400, in accordance with another embodiment of the present invention, may be in electrical communications with controls 204. Further, controls 204 may be in electrical communications with a filter 208. The filter tuner hardware 300, 400 is described in further detail below, but generally, the hardware 300, 400 may operate to monitor the accuracy of the filter 208 and cause adjustments to the filter 208 to set or maintain its accuracy. Controls 204 may include one or more processors, digital signal processors ("DSPs"), or other circuitry elements that may control the adjustment or accuracy of the filter 208 in response to signals communicated with the filter tuner hardware 300, 400. The filter 208 may be one or more of a variation of RC continuous-time filters such as, for example, a variation of a low-pass, or band-pass filter.

As shown in FIG. 2B, in contrast to the application depicted in FIG.2A, the filter tuner hardware 300, 400 may include logic 210. Internal logic 210 may consist of one of various forms of logic circuitry such as microprocessors, programmable logic controllers ("PLCs"), or other forms of logic circuitry. Additionally, internal logic 210 may include memory (e.g., ROM or EPROM) that contains executable code, firmware, or other forms of software that is processed by internal logic 210. Internal logic 210 may typically be located with filter tuner hardware 300, 400, but the logic 210 may alternatively be located at some other location (not depicted) with the components of the filter tuning application.

Figure 3:
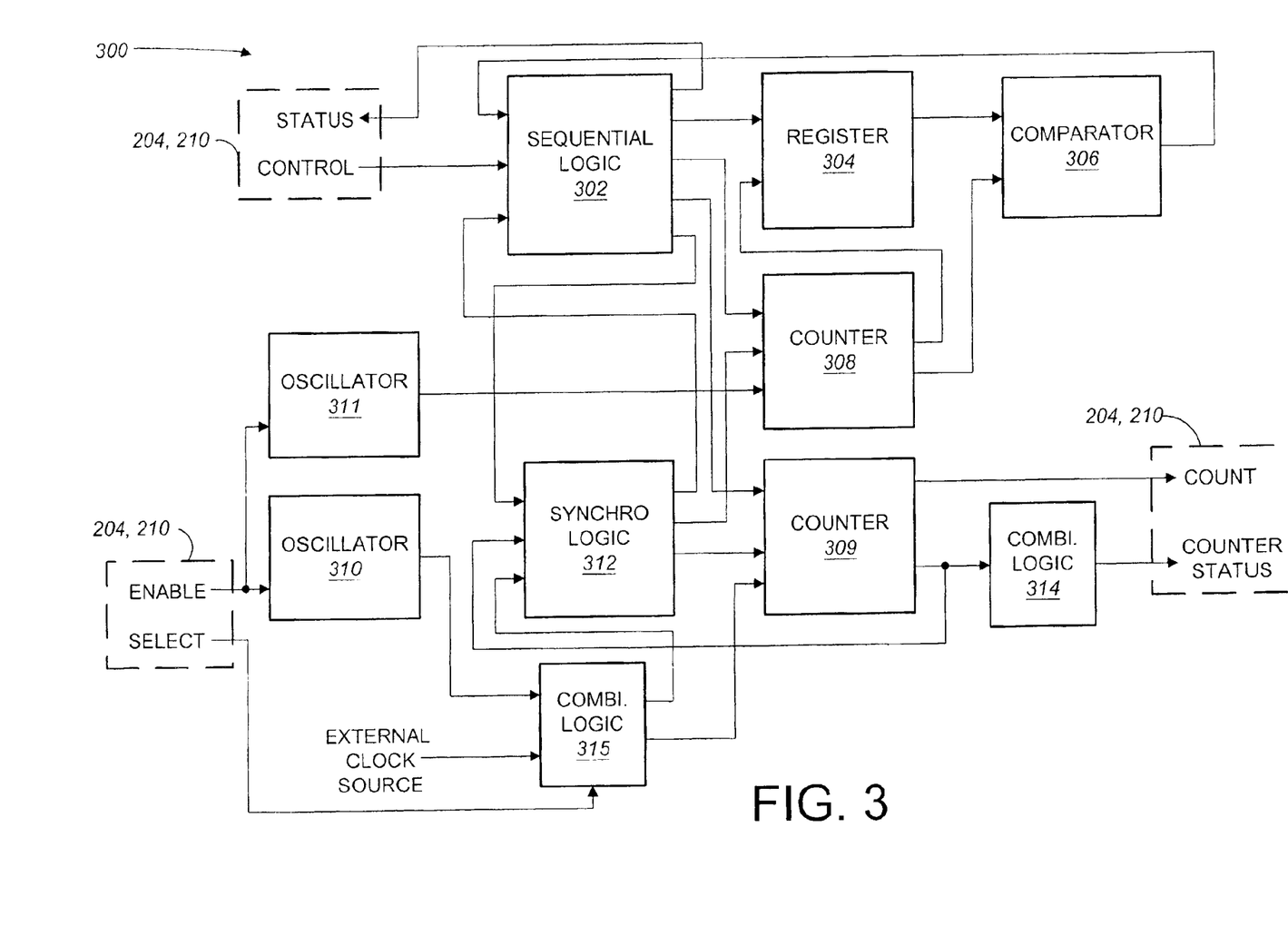
FIG. 3 is a block diagram representing a filter tuner hardware in accordance with embodiments of the present invention as presented in FIGS. 2A and 2B.

Focusing now on FIG. 3, there is shown a block diagram representing a filter tuner hardware 300 in accordance with embodiments of the present invention as presented in FIGS. 2A and 2B. The filter tuner hardware 300 may include several elements that are described in the following. It is noted that although single line connections are depicted between elements of the filter tuner hardware 300 to facilitate the description of the embodiments, a single-line may represent one or more connections and/or connecting circuits within the scope of the embodiments of the present invention.

The filter tuner hardware 300 may include a sequential logic 302 that has one or more inputs and outputs. The sequential logic 302 may transmit control and/or data signals ("signals") to other elements that make up the filter tuner hardware 300 The sequential logic 302 may also transmit signals to controls 204 (FIG. 2A). The transmitting of signals from the sequential logic 302 may occur in response to signals inputted to the sequential logic 302 from other elements of the filter tuner hardware 300 or from controls 204. The signals inputted from controls 204 may be inputted in response to the execution of filter tuner firmware 210 (FIG. 2A), in accordance with an embodiment of the present invention. Alternatively, the transmitting signals from the sequential logic 302 may occur in response to signals inputted to the sequential logic 302 from internal logic 210 (FIG. 2B), in accordance with another embodiment of the present invention.

As shown in FIG. 3, the sequential logic 302, in accordance with an embodiment of the present invention, may have inputs connected to one or more elements of the filter tuner hardware 300 including a comparator 306 and a synchronizing logic 312. The sequential logic 302, in accordance with an embodiment of the present invention, may also have outputs connected to one or more elements of the filter tuner hardware 300 including a register 304, a first counter 308, a second counter 309, and a synchronizing logic 312. Additionally, in accordance with an embodiment of the present invention, the sequential logic 302 may also transmit and receive signals from controls 204 (FIG. 2A). Alternatively, in accordance with another embodiment of the present invention, the sequential logic 302 may transmit or receive signals from internal logic 210 (FIG. 2B) and also transmit signals to controls 204.

The sequential logic 302 of the filter tuner hardware 300 may include one or more sequential logic circuits. For example, the sequential logic 302 may include one or more latches or flip-flops along with one or more combinational logic elements. As another example, the sequential logic 302 may include a state machine circuit. The sequential logic 302 may include other forms of sequential logic circuits within the scope of the embodiments of the present invention, as will be apparent to one skilled in the art.

Continuing with reference to FIG. 3, the filter tuner hardware 300 may also include a register 304. The register 304 may store signals that are inputted from elements of the filter tuner hardware 300 and transmit the stored signals to other elements of the filter tuner hardware 300. The inputting of signals to the register 304 for storage (i.e., loading the register) and the transmitting of stored signals from the register 304 may occur in response to signals inputted to the register 304 from other elements of the filter tuner hardware 300 or from controls 204. The signals inputted from controls 204 may be inputted in response to the execution of filter tuner firmware 206 (FIG. 2A), in accordance with an embodiment of the present invention. Alternatively, the inputting of signals to the register 304 for the storage and transmitting of stored signals from the register 304 may occur in response to signals inputted to the register 304 from internal logic 210 (FIG. 2B), in accordance with another embodiment of the present invention.

The register 304, in accordance with an embodiment of the present invention, may have inputs connected to one or more elements of the filter tuner hardware 300 including a sequential logic 302 and a first counter 308. The register 304, in accordance with an embodiment of the present invention, may also have outputs connected to one or more elements of the filter tuner hardware 300 including a comparator 306.

The register 304 of the filter tuner hardware 300 may include one or more sequential logic circuits. For example, the register 304 may include one or more latches or flip-flops along with one or more combinational logic elements. The register 304 may include other forms of sequential logic circuits within the scope of the embodiments of the present invention, as will be apparent to one skilled in the art.

The filter tuner hardware 300 of FIG. 3 may also include a comparator 306. The comparator 306 may generate an output signal in response to a comparison of the signals inputted to the comparator 306. For example, if the all of the signals inputted to the comparator 306 are equivalent, the comparator 306 may generate a particular output signal that indicates that status.

The comparator 306, in accordance with an embodiment of the present invention, may have inputs connected to one or more elements of the filter tuner hardware 300 including a register 304 and a first counter 308. The comparator 306, in accordance with an embodiment of the present invention, may also have one or more outputs connected to one or more elements of the filter tuner hardware 300 including a sequential logic 302.

The comparator 306 of the filter tuner hardware 300 may include one or more combinational logic elements that form one or more combinational logic circuits. For example, the comparator 306 may include one or more logic OR, AND, or NOT gates. The comparator 306 may include other types of combinational logic elements within the scope of the embodiments of the present invention, as will be apparent to one skilled in the art.

The filter tuner hardware 300 may also include a first counter 308 and a second counter 309. The first and second counters 308, 309 may output a one or more bit (i.e., multiple-bit) counting sequence (e.g., 000, 001, 010, . . . , 000, 001, 010, . . . in binary format) in response to signals inputted from other elements of the filter tuner hardware 300. For example the counters 308, 309 may count in response to one or more oscillating signal inputs. Also, the counters 308, 309 may output a counting sequence that is established based on signals that are loaded to the counters from other elements of the filter tuner hardware 300.

The counters 308, 309, in accordance with an embodiment of the present invention, may have inputs connected to one or more elements of the filter tuner hardware 300 including a sequential logic 302, a synchronizing logic 312, a second oscillator 311, and a second combinational logic 315. The counters 308, 309, in accordance with an embodiment of the present invention, may also have outputs connected to one or more elements of the filter tuner hardware 300 including a comparator 306 and a first combinational logic 314. Additionally, in accordance with an embodiment of the present invention, the counters 308, 309 may also transmit or receive signals from controls 204 (FIG. 2A). Alternatively, in accordance with another embodiment of the present invention, the counters 308, 309 may transmit or receive signals from internal logic 210 (FIG. 2B) and also transmit signals to controls 204.

The counters 308, 309 of the filter tuner hardware 300 may include one or more sequential logic circuits. For example, the counters 308, 309 may include one or more latches or flip-flops along with one or more combinational logic elements. The counters 308, 309 may include other forms of sequential logic circuits within the scope of the embodiments of the present invention, as will be apparent to one skilled in the art.

The filter tuner hardware 300 may also include a first oscillator 310 and a second oscillator 311. The first and second oscillators 310, 311 may generate an oscillating signal output that may be utilized for example to "clock" other sequential circuit elements of the filter tuner hardware 300, such as the counters 308, 309. The oscillators 310, 311 may generate output signals in response to input signals from controls 204 which may be inputted in response to the execution of filter tuner firmware 206 (FIG. 2A), in accordance with an embodiment of the present invention. Alternatively, the oscillators 310, 311 may generate output signals in response to input signals from internal logic 210 (FIG. 2B), in accordance with another embodiment of the present invention.

The oscillators 310, 311, in accordance with an embodiment of the present invention, may have outputs connected to one or more elements of the filter tuner hardware 300 including a first counter 308 and a second combinational logic 315. Additionally, in accordance with an embodiment of the present invention, the oscillators 310, 311 may also receive signals from controls 204 (FIG. 2A). Alternatively, in accordance with another embodiment of the present invention, the oscillators 310, 311 may receive signals from internal logic 210 (FIG. 2B).

The oscillators 310, 311 may include one or more circuit elements. For example, the oscillators 310, 311 may include one or more resistance or capacitance elements. As another example, the oscillators 310, 311 may include a quartz crystal that generates an oscillating signal at one or more frequencies. Additionally, the oscillators 310, 311 may include one or more analog-to-digital ("A/D") conversion circuitries that may convert an analog oscillating signal generated, for example, from a quartz crystal to a digital oscillating signal (e.g., a square wave). The oscillators 310, 311 may include other forms of circuitry within the scope of the embodiments of the present invention, as will be apparent to one skilled in the art.

In further reference to FIG. 3, the filter tuner hardware 300 may also include a synchronizing logic 312. The synchronizing logic 312 may synchronize signals that are inputted from elements of the filter tuner hardware 300 so that the outputted signals are in synchronism with signals from other elements of the filter tuner hardware 300. In performing such a synchronizing function, the synchronizing logic 312 may utilize one or more synchronous signals generated by elements of the filter tuner hardware 300 such as, for example, the oscillating signals that may be generated by the first and second oscillators 310, 311.

The synchronizing logic 312, in accordance with an embodiment of the present invention, may have inputs connected to one or more elements of the filter tuner hardware 300 including a sequential logic 302, a second counter 309, and a second combinational logic 315. The synchronizing logic 312, in accordance with an embodiment of the present invention, may also have outputs connected to one or more elements of the filter tuner hardware 300 including a sequential logic 302 and a first and second counter 308, 309.

The synchronizing logic 312, of the filter tuner hardware 300 may include one or more sequential logic circuits. For example, the synchronizing logic 312, may include one or more latches or flip-flops along with one or more combinational logic elements. The synchronizing logic 312 may include other forms of sequential logic circuits within the scope of the embodiments of the present invention, as will be apparent to one skilled in the art.

The filter tuner hardware 300 may also include a first combinational logic 314 and a second combinational logic 315. The first and second combinational logic 314, 315 may process signals such that certain output signals are provided in response to certain input signals. For example, the combinational logic 314, 315 may provide logic functions such as OR, AND, NOT, or combinations of these logic functions upon inputted signals. The combinational logical 314, 315 may also provide certain output signals in further response to signals inputted to the combinational logic 314, 315 from controls 204 (FIG. 2A) that may respond to the execution of filter tuner firmware 206 (FIG. 2A), in accordance with an embodiment of the present invention. Alternatively, the combinational logical 314, 315 may also provide certain output signals in further response to signals inputted to the combinational logic 314, 315 from internal logic 210 (FIG. 2B), in accordance with another embodiment of the present invention.

The combinational logic 314, 315, in accordance with an embodiment of the present invention, may have inputs connected to one or more elements of the filter tuner hardware 300 including a first counter 309 and a first oscillator 310. Additionally, the combinational logic 314, 315 may have inputs connected to one or more external clock sources which may be used to provide reference clock signals for the purpose of testing the operation of the filter tuner hardware 300. The combinational logic 314, 315, in accordance with an embodiment of the present invention, may also have outputs connected to one or more elements of the filter tuner hardware 300 including a first counter 309 and a synchronizing logic 312. Additionally, in accordance with an embodiment of the present invention, the combinational logic 314, 315 may also transmit and receive signals from controls 204 (FIG. 2A). Alternatively, in accordance with another embodiment of the present invention, the combinational logic 314, 315 may transmit or receive signals from internal logic 210 (FIG. 2B) and also transmit signals to controls 204.

The combinational logic 314, 315 of the filter tuner hardware 300 may include one or more combinational logic elements that form one or more combinational logic circuits. For example, the combinational logic 314, 315 may include one or more logic OR, AND, or NOT gates. The combinational logic 314, 315 may include other types of combinational logic elements within the scope of the embodiments of the present invention, as will be apparent to one skilled in the art.

As discussed above with respect to elements of the filter tuner hardware 300 depicted in FIG. 3, several of these elements may receive and/or transmit signals to controls 204 (FIG. 2A), in accordance with an embodiment of the present invention. Further, signals received from and/or transmitted to controls 206 may be responsive to the execution of filter tuner firmware 206 (FIG. 2A). For example, as depicted in FIG. 3, the sequential logic 302 may receive control signals from controls 204 in response to execution of filter tuner firmware 206. Further, the sequential logic 302 may transmit status signals to controls 204. As another example, the first and second oscillators 310, 311 may receive enable inputs from controls 204 and the second combinational logic 315 may receive a select input from controls 204 also. As another example, the second counter 309 may transmit a count output to controls 204 and the first combinational logic 314 may transmit a counter status output to controls 204.

Alternatively, in accordance with another embodiment of the present invention, several elements of the filter tuner hardware 300 may receive and/or transmit signals to internal logic 210 (FIG. 2B) and/or transmit signals to controls 204 (FIG. 2A) which may be responsive to the execution of filter tuner firmware 206 (FIG. 2A). For example, as depicted in FIG. 3, the sequential logic 302 may receive control signals from internal logic 210. Further, the sequential logic 302 may transmit status signals to controls 204. As another example, the first and second oscillators 310, 311 may receive enable inputs from internal logic 210 and the second combinational logic 315 may receive a select input from internal logic 210 also. As another example, the second counter 309 may transmit a count output to controls 204 and the first combinational logic 314 may transmit a counter status to internal logic 210.

Figure 4:
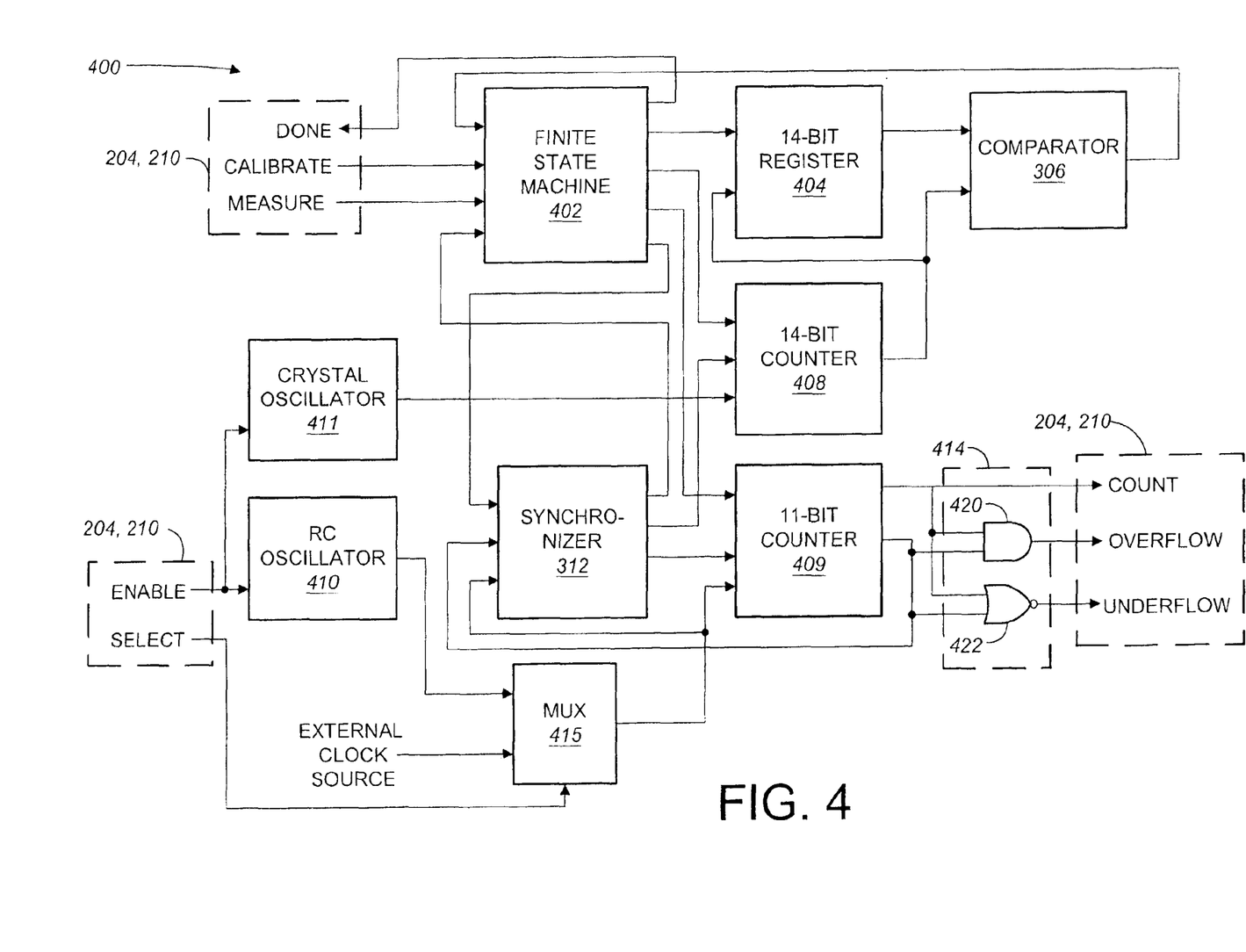
FIG. 4 is a block diagram representing a filter tuner hardware in accordance with other embodiments of the present invention as presented in FIGS. 2A and 2B.

Focusing now on FIG. 4, there is shown a block diagram representing a filter tuner hardware 400 in accordance with other embodiments of the present invention as presented in FIGS. 2A and 2B. The filter tuner hardware 400 may include several elements that are described in the following. It is noted that although single line connections are depicted between elements of the filter tuner hardware 400 to facilitate the description of the embodiments, a single-line may represent one or more connections and/or connecting circuits within the scope of the embodiments of the present invention.

The filter tuner hardware 400 may include a finite state machine 402, that has one or more inputs and outputs. The finite state machine 402 may transmit signals to other elements that make up the filter tuner hardware 400 The finite state machine 402 may also transmit signals to controls 204 (FIG. 2A). The transmitting of signals from the finite state machine 402 may occur in response to signals inputted to the finite state machine 402 from other elements of the filter tuner hardware 400 or from controls 204. The signals inputted from controls 204 may be inputted in response to the execution of filter tuner firmware 206 (FIG. 2A), in accordance with an embodiment of the present invention. Alternatively, the transmitting of signals from the finite state machine 402 may occur in response to signals inputted to the finite state machine 402 from internal logic 210 (FIG. 2B), in accordance with another embodiment of the present invention.

As shown in FIG. 4, the finite state machine 402, in accordance with an embodiment of the present invention, may have inputs connected to one or more elements of the filter tuner hardware 400 including a comparator 306 and a synchronizer 412. The finite state machine 402, in accordance with an embodiment of the present invention, may also have outputs connected to one or more elements of the filter tuner hardware 400 including a 14-bit register 404, a 14-bit counter 408, an 11-bit counter 409, and a synchronizer 412. Additionally, in accordance with an embodiment of the present invention, the finite state machine 402 may also transmit and receive signals from controls 204 (FIG. 2A). Alternatively, in accordance with another embodiment of the present invention, the finite state machine 402 may transmit or receive signals from internal logic 210 (FIG. 2B) and also transmit signals to controls 204.

The finite state machine 402 of the filter tuner hardware 400 may include one or more sequential logic elements and one or more combinational logic elements. For example, the finite state machine 402 may include one or more latches or flip-flops and one or more logic function elements such as OR, AND, or NOT gates. The finite state machine 402 may include other forms of sequential logic elements and combinational logic elements within the scope of the embodiments of the present invention, as will be apparent to one skilled in the art.

Continuing with reference to FIG. 4, the filter tuner hardware 400 may also include a 14-bit register 404. The 14-bit register 404 may store signals of up to 14-bit lengths that are inputted from elements of the filter tuner hardware 400 and transmit the stored signals to other elements of the filter tuner hardware 400. The inputting of signals to the 14-bit register 404 for storage (i.e., loading the register) and the transmitting of stored signals from the 14-bit register 404 may occur in response to signals inputted to the 14-bit register 404 from other elements of the filter tuner hardware 400 or from controls 204. The signals inputted from controls 204 may be inputted in response to the execution of filter tuner firmware 206 (FIG. 2A), in accordance with an embodiment of the present invention. Alternatively, the inputting of signals to the 14-bit register 404 for the storage and transmitting of stored signals from the 14-bit register 404 may occur in response to signals inputted to the 14-bit register 404 from internal logic 210 (FIG. 2B), in accordance with another embodiment of the present invention.

The 14-bit register 404, in accordance with an embodiment of the present invention, may have inputs connected to one or more elements of the filter tuner hardware 400 including a finite state machine 402 and a 14-bit counter 408. The 14-bit register 404, in accordance with an embodiment of the present invention, may also have outputs connected to one or more elements of the filter tuner hardware 400 including a comparator 306.

The 14-bit register 404 of the filter tuner hardware 400 may include one or more sequential logic circuits. For example, the 14-bit register 404 may include a cascaded circuit of 14 latches or flip-flops electrically coupled to one or more combinational logic elements. The 14-bit register 404 may include other forms of sequential logic circuits within the scope of the embodiments of the present invention, as will be apparent to one skilled in the art.

The filter tuner hardware 400 of FIG. 4 may also include a comparator 306. The comparator 306 may generate an output signal in response to a comparison of the signals inputted to the comparator 306. For example, if the all of the signals inputted to the comparator 306 are equivalent, the comparator 306 may generate a particular output signal that indicates that status.

The comparator 306, in accordance with an embodiment of the present invention, may have inputs connected to one or more elements of the filter tuner hardware 400 including a 14-bit register 404 and a 14-bit counter 408. The comparator 306, in accordance with an embodiment of the present invention, may also have one or more outputs connected to one or more elements of the filter tuner hardware 400 including a finite state machine 402.

The comparator 306 of the filter tuner hardware 400 may include one or more combinational logic elements that form one or more combinational logic circuits. For example, the comparator 306 may include one or more logic OR, AND, or NOT gates. The comparator 306 may include other types of combinational logic elements within the scope of the embodiments of the present invention, as will be apparent to one skilled in the art.

The filter tuner hardware 400 may also include a 14-bit counter 408 and an 11-bit counter 409. The 14-bit counter 408 may output up to a 14-bit counting sequence in response to signals inputted from other elements of the filter tuner hardware 400. Similarly, the 11-bit counter 409 may output up to an 11-bit counting sequence in response to signals inputted from other elements of the filter tuner hardware 400. For example either of the counters 408, 409 may count in response to one or more oscillating signal inputs. Also, both counters 408, 409 may output a counting sequence that is established based on multiple-bit signals that are loaded to the counters from other elements of the filter tuner hardware 400.

The counters 408, 409, in accordance with an embodiment of the present invention, may have inputs connected to one or more elements of the filter tuner hardware 400 including a finite state machine 402, a synchronizer 412, a crystal oscillator 411, and a multiplexer 415. The counters 408, 409, in accordance with an embodiment of the present invention, may also have outputs connected to one or more elements of the filter tuner hardware 400 including a comparator 306 and a combinational logic 414. Additionally, in accordance with an embodiment of the present invention, the counters 408, 409 may also transmit or receive signals from controls 204 (FIG. 2A). Alternatively, in accordance with another embodiment of the present invention, the counters 408, 409 may transmit or receive signals from internal logic 210 (FIG. 2B) and also transmit signals to controls 204.

The counters 408, 409 of the filter tuner hardware 400 may include one or more sequential logic circuits. For example, the 14-bit counter 408 may include a cascaded circuit of 14 latches or flip-flops electrically coupled to one or more combinational logic elements. Similarly, for example, the 11-bit counter 409 may include a cascaded circuit of 11 latches or flip-flops electrically coupled to one or more combinational logic elements. The counters 408, 409 may include other forms of sequential logic circuits within the scope of the embodiments of the present invention, as will be apparent to one skilled in the art.

The filter tuner hardware 400 may also include an RC oscillator 410 and a crystal oscillator 411. Both oscillators 410, 411 may generate an oscillating signal output that may be utilized for example to "clock" other sequential circuit elements of the filter tuner hardware 400, such as the counters 408, 409. The oscillators 410, 411 may generate output signals in response to input signals from controls 204 which may be inputted in response to the execution of filter tuner firmware 206 (FIG. 2A), in accordance with an embodiment of the present invention. Alternatively, the oscillators 410, 411 may generate output signals in response to input signals from internal logic 210 (FIG. 2B), in accordance with another embodiment of the present invention.

The oscillators 410, 411, in accordance with an embodiment of the present invention, may have outputs connected to one or more elements of the filter tuner hardware 400 including a 14-bit counter 408 and a multiplexer 415. Additionally, in accordance with an embodiment of the present invention, the oscillators 410, 411 may also receive signals from controls 204 (FIG. 2A). Alternatively, in accordance with another embodiment of the present invention, the oscillators 410, 411 may receive signals from internal logic 210 (FIG. 2B).

The RC oscillator may include one or more resistance elements and one or more capacitance elements electrically coupled to provide a circuit that may generate an oscillating signal output. The crystal oscillator 411 may include one or more crystals, for example quartz crystals, coupled to other circuit elements (e.g., resistance or capacitance elements) to provide a circuit that may generate an oscillating signal output. Additionally, the oscillators 410, 411 may include one or more analog-to-digital ("A/D") conversion circuitries that may convert a generated analog oscillating signal to a digital oscillating signal (e.g., a square wave). The oscillators 410, 411 may also include other forms of circuitry within the scope of the embodiments of the present invention, as will be apparent to one skilled in the art.

In further reference to FIG. 4, the filter tuner hardware 400 may also include a synchronizer 412. The synchronizer 412 may synchronize signals that are inputted from elements of the filter tuner hardware 400 so that the outputted signals are in synchronism with signals from other elements of the filter tuner hardware 400. In performing such a synchronizing function, the synchronizer 412 may utilize one or more synchronous signals generated by elements of the filter tuner hardware 400 such as, for example, the oscillating signals that may be generated by the oscillators 410, 411.

The synchronizer 412, in accordance with an embodiment of the present invention, may have inputs connected to one or more elements of the filter tuner hardware 400 including a finite state machine 402, an 11-bit counter 409, and a multiplexer 415. The synchronizer 412, in accordance with an embodiment of the present invention, may also have outputs connected to one or more elements of the filter tuner hardware 400 including a finite state machine 402, a 14-bit counter 408, and an 11-bit counter 409.

The synchronizer 412, of the filter tuner hardware 400 may include one or more sequential logic circuits. For example, the synchronizer 412, may include one or more latches or flip-flops electrically coupled to one or more combinational logic elements. The synchronizer 412 may include other forms of sequential logic circuits within the scope of the embodiments of the present invention, as will be apparent to one skilled in the art.

The filter tuner hardware 400 may also include a combinational logic 414. The combinational logic 414 may provide counter overflow and underflow status signals in response to input signals from the 11-bit counter 409.

The combinational logic 414, in accordance with an embodiment of the present invention, may have inputs connected to one or more elements of the filter tuner hardware 400 including an 11-bit counter 409. Additionally, in accordance with an embodiment of the present invention, the combinational logic 414 may also transmit signals to controls 204 (FIG. 2A). Alternatively, in accordance with another embodiment of the present invention, the combinational logic 414 may transmit to internal logic 210 (FIG. 2B) and to controls 204.

The combinational logic 414, in accordance with an embodiment of the present invention, may include a logic AND gate 420 and a logic NOR gate 422 that are electrically coupled. The combinational logic 414 may alternatively include other types of combinational logic elements configured to provide counter overflow and underflow status signals within the scope of the embodiments of the present invention, as will be apparent to one skilled in the art.

The filter tuner hardware 400 may also include a multiplexer 415. The multiplexer 415 may selectively output one of a plurality of signals inputted to the multiplexer 415. The multiplexer 415 may selectively output one of a plurality of input signals in response to signals inputted to the multiplexer 415 from controls 204 (FIG. 2A) that may respond to the execution of filter tuner firmware 206 (FIG. 2A), in accordance with an embodiment of the present invention. Alternatively, the multiplexer 415 may selectively output one of a plurality of input signals in response to signals inputted to the multiplexer 415 from internal logic 210 (FIG. 2B), in accordance with another embodiment of the present invention.

The multiplexer 415, in accordance with an embodiment of the present invention, may have inputs connected to one or more elements of the filter tuner hardware 400 including an RC oscillator 410. Additionally, the multiplexer 415 may have inputs connected to one or more external clock sources which may be used to provide reference clock signals for the purpose of testing the operation of the filter tuner hardware 400. The multiplexer 415, in accordance with an embodiment of the present invention, may also have outputs connected to one or more elements of the filter tuner hardware 400 including an 11-bit counter 409 and a synchronizer 412. Additionally, in accordance with an embodiment of the present invention, the multiplexer 415 may also receive signals from controls 204 (FIG. 2A). Alternatively, in accordance with another embodiment of the present invention, the multiplexer 415 may receive signals from internal logic 210 (FIG. 2B) and also transmit signals to controls 204.

The multiplexer 415 of the filter tuner hardware 400 may include one or more combinational logic elements that form one or more combinational logic circuits to provide multiplexing functionality. For example, the multiplexer 415 may include one or more logic OR, AND, or NOT gates. The multiplexer 415 may include other types of combinational logic elements within the scope of the embodiments of the present invention, as will be apparent to one skilled in the art.

As discussed above with respect to elements of the filter tuner hardware 400 depicted in FIG. 4, several of these elements may receive and/or transmit signals to controls 204 (FIG. 2A), in accordance with an embodiment of the present invention. Further, signals received from and/or transmitted to controls 206 may be responsive to the execution of filter tuner firmware 206 (FIG. 2A). For example, as depicted in FIG. 4, the finite state machine 402 may receive control signals to execute a calibration cycle (i.e., "CALIBRATE") or a measurement cycle (i.e., "MEASURE") from controls 204 in response to execution of filter tuner firmware 206. Further, the finite state machine 402 may transmit status signals indicating that a calibration or measurement cycle is done (i.e., "DONE") to controls 204. As another example, the RC oscillator 410 and the crystal oscillator 411 may receive enable inputs from controls 204 and the multiplexer 415 may receive a select input from controls 204 also. As another example, the 11-bit counter 409 may transmit a count output to controls 204 and the combinational logic 414 may transmit a counter overflow status output or counter underflow status output to controls 204.

Alternatively, in accordance with another embodiment of the present invention, several elements of the filter tuner hardware 400 may receive and/or transmit signals to internal logic 210 (FIG. 2B) and/or transmit signals to controls 204 (FIG. 2A) which may be responsive to the execution of filter tuner firmware 206 (FIG. 2A). For example, as depicted in FIG. 4, the finite state machine 402 may receive control signals to execute a calibration cycle (i.e., "CALIBRATE") or a measurement cycle (i.e., "MEASURE") from internal logic 210. Further, the finite state machine 402 may transmit status signals indicating that a calibration or measurement cycle is done (i.e., "DONE") to internal logic 210. As another example, the RC oscillator 410 and the crystal oscillator 411 may receive enable inputs from internal logic 210 and the multiplexer 415 may receive a select input from internal logic 210 also. As another example, the 11-bit counter 409 may transmit a count output to controls 204 and the combinational logic 414 may transmit a counter overflow status output or counter underflow status output to internal logic 210.

As discussed above with respect to elements of the filter tuner hardware 300, 400 depicted in FIGS. 3 and 4, several of these elements may receive and/or transmit signals to controls 204 (FIG. 2A), in accordance with an embodiment of the present invention. Additionally, signals received from and/or transmitted to controls 206 may be responsive to the execution of filter tuner firmware 206 (FIG. 2A). Further, as discussed above with respect to elements of the filter tuner hardware 300, 400 depicted in FIGS. 3 and 4, several of these elements may receive and/or transmit signals to internal logic 210 (FIG. 2B) and/or transmit signals to controls 204 which may be responsive to the execution of filter tuner firmware 206, in accordance with another embodiment of the present invention. In this regard, the following descriptions will present methods, in accordance with embodiments of the present invention, that may be executed by filter tuner firmware 206 and/or internal logic 210 in conjunction with the filter tuner hardware 300, 400, controls 204, and filter 208 in, for example, applications such as those depicted in FIGS. 2A and 2B. It is noted, though, that references made to elements of FIGS. 2A, 2B, 3, and 4 in describing the following methods are made merely to facilitate the description of the embodiments of the present invention, and the utilization of the methods is not limited to applications with these elements.

Figure 5:
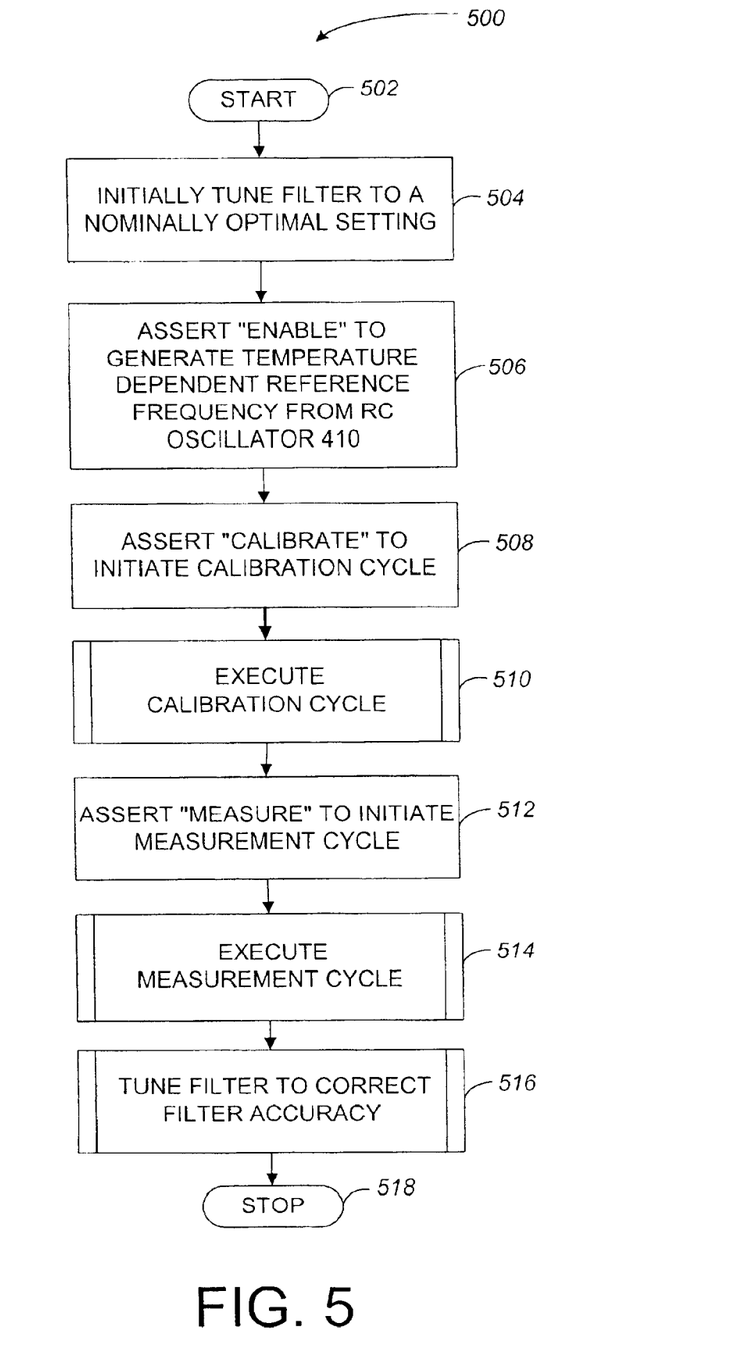
FIG. 5 is a flowchart diagram representing a method for a filter tuner in accordance with embodiments of the present invention.

Focusing now on FIG. 5, a flowchart diagram is shown representing a method 500 for a filter tuner in accordance with embodiments of the present invention. The method 500 begins at start step 502. Following start step 502, in step 504, a filter 208 is tuned to a nominally optimal setting. A nominally optimal setting may be, for example, a setting at which the filter will have −1.0 dB loss at the nominal filter cutoff frequency. The determination of a nominally optimal initial setting for the filter may be made by execution of filter tuner firmware 206, in accordance with an embodiment of the present invention. In accordance with another embodiment of the present invention, the setting determination may be made by internal logic 210. The filter setting may be represented by one or more coarse tuning bits and by one or more fine tuning bits. For example, the filter setting may be represented by 6-bits for coarse-tuning and 6-bits for fine-tuning (i.e., a 12-bit setting).

In further regard to step 504 of the method 500, the setting of the filter 208 may be made using control words transmitted to controls 204 from filter tuner firmware 206, in accordance with an embodiment of the present invention, or from internal logic 210, in accordance with another embodiment of the present invention. For example, a low-pass cutoff control word may be designated "TXF" and a high-pass cutoff control word may be designated "RXF." Each control word (TXF, RXF) may be monotonic with higher frequency cutoffs being indicated by higher binary numbers. In response to the control words, the controls 204 may cause adjustments to the appropriate components of the filter 208 to occur which results in the tuning of the filter 208 to a nominally optimal setting.

Following step 504, in step 506, the enable input to the RC oscillator 410 is asserted in order to generate a temperature dependent reference frequency to drive the 11-bit counter 409. The enable input of the RC oscillator may be asserted by signals from controls 204 in response to execution of filter tuner firmware 206, in accordance with an embodiment of the present invention, or by signals from internal logic 210, in accordance with another embodiment of the present invention. When enabled, the RC oscillator may operate at some nominal frequency such as, for example, 10 MHz. Although not shown in step 506, as discussed above, an enable input may also be transmitted to the crystal oscillator 411 to enable it to provide oscillating signals.

Following step 506, in step 508, the "CALIBRATE" control word is asserted to initiate a calibration cycle by the filter tuner hardware 400. The assertion of "CALIBRATE" may be made by filter tuner firmware 206, in accordance with an embodiment of the present invention, or by internal logic 210, in accordance with another embodiment of the present invention. Following step 508, in step 510, a calibration cycle is executed by the filter tuner hardware 400. The steps involved in this execution step 510 are described below with regard to FIG. 6.

Following step 510, in step 512, the "MEASURE" control word is asserted to initiate a measurement cycle by the filter tuner hardware 400. The assertion of "MEASURE" may be made by filter tuner firmware 206, in accordance with an embodiment of the present invention, or by internal logic 210, in accordance with another embodiment of the present invention. Following step 512, in step 514, a measurement cycle is executed by the filter tuner hardware 400. The steps involved in this execution step 514 are described below with regard to FIG. 7.

Following step 514, in step 516, the filter 208 is tuned to correct the accuracy of the filter cutoff frequency. The steps involved in this execution step 516 are described below with regard to FIG. 8. Following step 516 is the stop step 518 at which the method 500 is complete.

Figure 6:
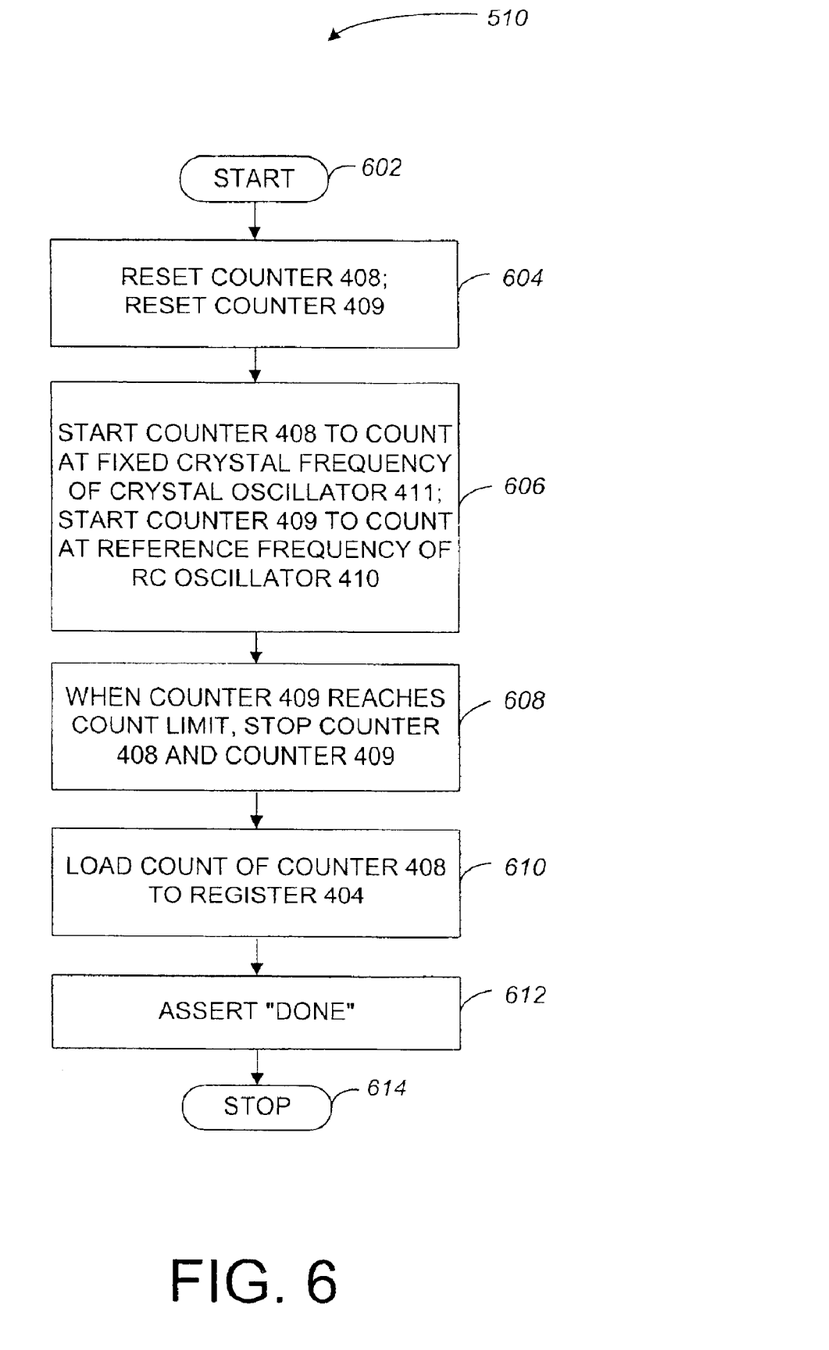
FIG. 6 is a flowchart diagram further representing a method for a filter tuner in accordance with embodiments of the present invention as presented in FIG. 5.

Focusing now on FIG. 6, a flowchart diagram is shown further representing a method 510 for a filter tuner in accordance with embodiments of the present invention as presented in FIG. 5. Specifically a method 510 for execution of the calibration cycle of the method 500 (FIG. 5) is represented in accordance with embodiments of the present invention. The method 510 begins at start step 602. Following start step 602, in step 604, 14-bit counter 408 is reset and 11-bit counter 409 is reset, for example, to zero. The input signals to the counters 408, 409 to execute the reset may be transmitted from the finite state machine 402.

Following step 604, in step 606, the counters 408, 409 are started. The counters 408, 409 may be started simultaneously, in accordance with embodiments of the present invention. The input signals to the counters 408, 409 to initiate counting may be transmitted from the synchronizer 412. When initiated, the 14-bit counter 408 may count at a fixed frequency generated by the crystal oscillator 411, which inputs an oscillating signal to the counter 408. The fixed frequency of the crystal oscillator 411 may be, for example, approximately 35 MHz, dependent on the characteristics of the crystal. When the 11-bit counter 409 is initiated to count, it may count at the temperature dependent reference frequency generated by the RC oscillator 410.

A brief reference to FIG. 4 shows that the RC oscillator 410 inputs an oscillating signal to the 11-bit counter 409 via the multiplexer 415, which also receives an input from an external clock source. As discussed above in the description of the filter tuner hardware 400, the multiplexer 415 may receive a select signal from either filter tuner firmware 206 (via controls 204) or from internal logic 210, in accordance with embodiments of the present invention. Thus, an oscillating signal may be transmitted to the 11-bit counter 409 from either the RC oscillator, under normal operation, or from an external clock source, under testing operation.

Continuing now with reference to FIG. 6, following step 606, in step 608 the counters 408, 409 are stopped when the 11-bit counter 409 reaches a predetermined count limit which may be, for example, 1024 counts. The counters 408, 409 may be stopped simultaneously, in accordance with embodiments of the present invention. The determination that the counter 409 has reached the count limit may be made based on the count status signals transmitted from the counter 409 to either controls 204 or to internal logic 210, in accordance with embodiments of the present invention. Once counter 409 has been determined to reach the count limit, signals from either controls 204 or internal logic 210 are transmitted to the filter tuner hardware 400 to stop the counting. The input signals to the counters 408, 409 to stop counting may be transmitted from the synchronizer 412.

Following step 608, in step 610, the count reached by the 14-bit counter 408, when it was stopped in step 608, is loaded to the 14-bit register 404. The load signal to the register 404 may be transmitted form the finite state machine 402 in response to input signals to the finite state machine 402 indicating that the 11-bit counter 409 has reached the predetermined count limit.

Following step 610, in step 612, the "DONE" control word is asserted to indicate that the calibration cycle is complete. The asserted "DONE" signal is transmitted from the finite state machine 402 to either controls 204 or internal logic 210, in accordance with embodiments of the present invention. Following step 612 is the stop step 614 at which the method 510 is complete.

Figure 7:
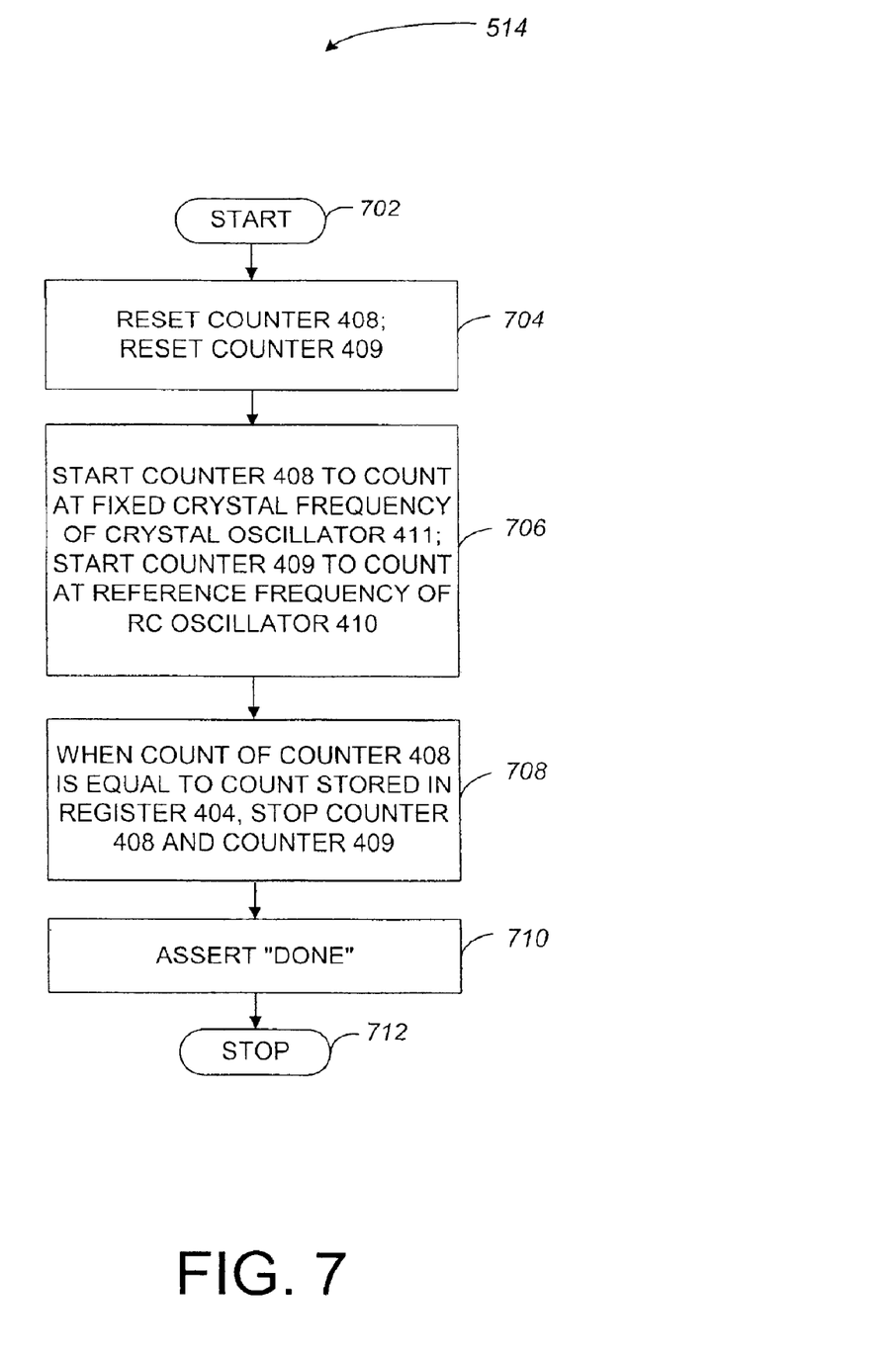
FIG. 7 is a flowchart diagram further representing a method for a filter tuner in accordance with embodiments of the present invention as presented in FIG. 5.

Focusing now on FIG. 7, a flowchart diagram is shown further representing a method 514 for a filter tuner in accordance with embodiments of the present invention as presented in FIG. 5. Specifically a method 514 for execution of the measurement cycle of the method 500 (FIG. 5) is represented in accordance with embodiments of the present invention. The method 514 begins at start step 702. Following start step 702, in step 704, 14-bit counter 408 is reset and 11-bit counter 409 is reset, for example, to zero. The input signals to the counters 408, 409 to execute the reset may be transmitted from the finite state machine 402.

Following step 704, in step 706, the counters 408, 409 are started. The counters 408, 409 may be started simultaneously, in accordance with embodiments of the present invention. The input signals to the counters 408, 409 to initiate counting may be transmitted from the synchronizer 412. When initiated, the 14-bit counter 408 may count at a fixed frequency generated by the crystal oscillator 411, which inputs an oscillating signal to the counter 408. The fixed frequency of the crystal oscillator 411 may be, for example, approximately 35 MHz, dependent on the characteristics of the crystal. When the 11-bit counter 409 is initiated to count, it may count at the temperature dependent reference frequency generated by the RC oscillator 410.

Following step 706, in step 708, the counters 408, 409 are stopped when the 14-bit counter 408 reaches a count equivalent to the count that is stored in the 14-bit register 404. The determination that the counter 408 has reached a count that is equivalent to the count stored in the register 404 may be based on the output signals from the comparator 306. As is shown, for example, in FIG. 4, the output of the register 404 and the counter 408 are both transmitted to the inputs of the comparator 306, and when these inputs to the comparator 306 are equivalent, an indicating signal may be transmitted from the comparator 306 to the finite state machine 402. In response, signals may be transmitted from the state machine 402 to the synchronizer 412, and the input signals to the counters 408, 409 to stop counting may subsequently be transmitted from the synchronizer 412.

Following step 708, in step 710, the "DONE" control word is asserted to indicate that the measurement cycle is complete. The asserted "DONE" signal is transmitted from the finite state machine 402 to either controls 204 or internal logic 210, in accordance with embodiments of the present invention. Following step 710 is the stop step 712 at which the method 514 is complete.

Figure 8:
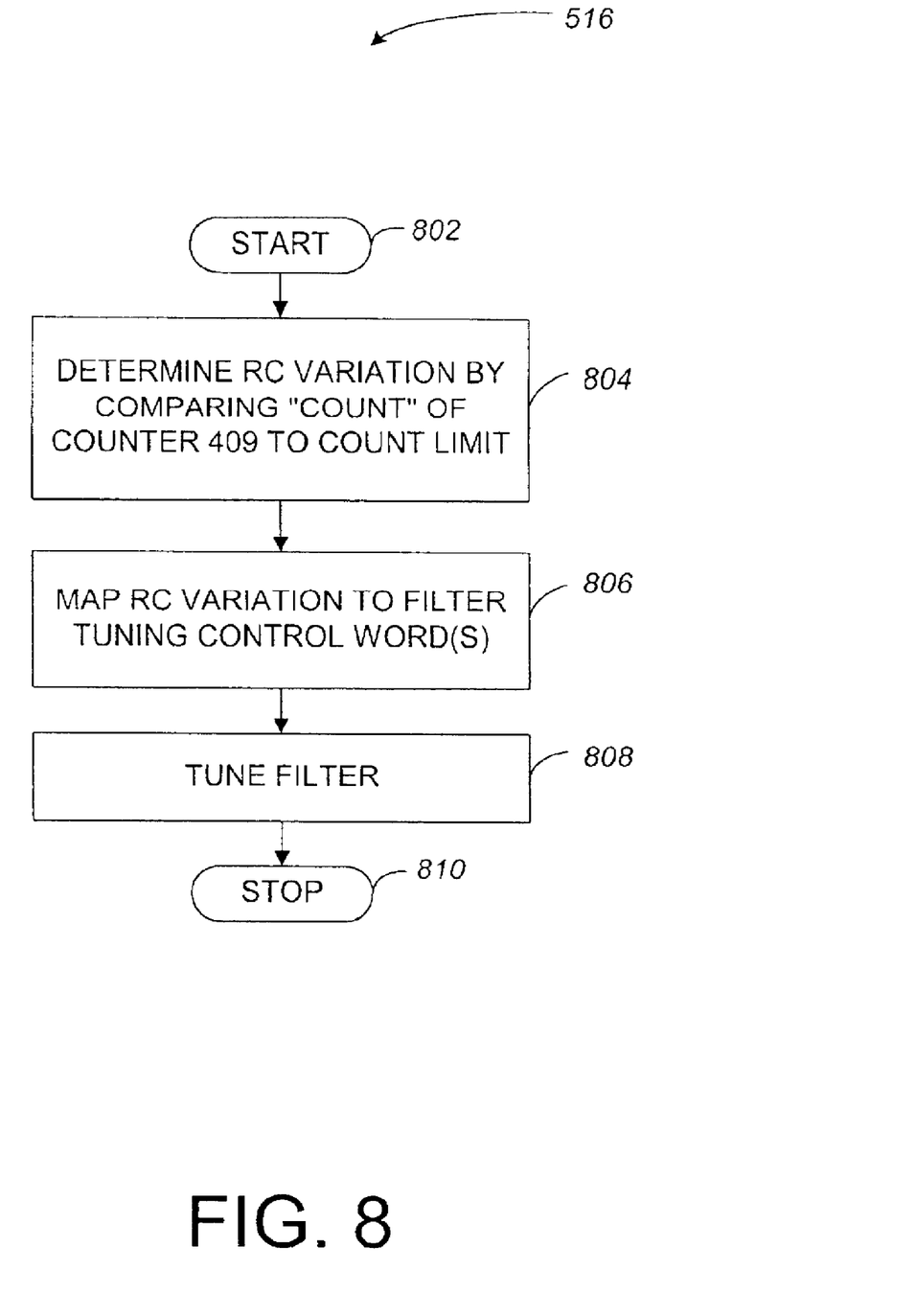
FIG. 8 is a flowchart diagram further representing a method for a filter tuner in accordance with embodiments of the present invention as presented in FIG. 5.

Focusing finally on FIG. 8, a flowchart diagram is shown further representing a method 516 for a filter tuner in accordance with embodiments of the present invention as presented in FIG. 5. Specifically a method 516 for tuning the filter 208 to correct the accuracy of the filter cutoff frequency in accordance with the method 500 (FIG. 5) is represented, in accordance with embodiments of the present invention. The method 516 begins at start step 802.

Following start step 802, in step 804, the variation of the resistance-capacitance ("RC") components of the filter 208 is determined. Since the temperature variation of the RC is dominated by the resistor in a filter 208 designed with, for example, High-resitivity Poly0 resistors and Interpoly capacitors, the determination of the variation of the RC is made by determining the variation of the resistance ("R"). Specifically, a percentage variation of R is determined by finding the difference of the count of counter 409, that is reached at step 708 (FIG. 7) of the measurement cycle, to the predetermined count referenced in step 608 (FIG. 6). The following equation may represent this determination:

$$R_{DIFF} = CNT_{CNTR\ 409} - CNT_{PRE-DET} \quad \text{(Eq. 1)}$$

The least significant bit ("LSB") of RDIFF from Eq. 1 approximately represents a 0.1% temperature variation in the RC of the RC oscillator 410, and the percentage change in the RC of the filter 208 is typically less than ±5%. Therefore, a percentage variation in the frequency of the RC oscillator 410 is approximately equal to a percentage change in the RC of the filter 208, particularly for small percentage variations.

Following step 804, in step 806, the RC variation determined in step 804 is mapped to the filter tuning control words TXF (low-pass control) and RXF (high-pass control). The following equations may represent this mapping:

$$TXF_{NEW} = TXF_{INIT} + R_{DIFF} * K_{TX} \quad \text{(Eq. 2)}$$

$$RXF_{NEW} = RXF_{INIT} + R_{DIFF} * K_{RX} \quad \text{(Eq. 3)}$$

In Eq. 2 and Eq. 3 above, the constants $K_{TX}$ and $K_{RX}$ may be values that are provided or determined for each nominal filter cutoff and these constants can have positive or negative values. To prevent changing the values of $K_{TX}$ and $K_{RX}$ too quickly, a certain amount of hysteresis may be introduced.

Following step 806, in step 808, the filter 208 is tuned. This tuning of the filter 208 may be made using the control words TXF and RXF transmitted to controls 204 from filter tuner firmware 206 or from internal logic 210, in accordance with embodiments of the present invention. In response to the control words, the controls 204 may cause adjustments to the appropriate components of the filter 208 to occur which results in the tuning of the filter 208 to correct cutoff frequency accuracy affected by temperature variation.

It is emphasized that references made to elements of FIGS. 2A, 2B, 3, and 4 in describing the preceding methods are made merely to facilitate the description of the embodiments of the present invention, and the utilization of the methods is not limited to applications with these elements. Further, the flowchart diagrams of the filter tuning methods 500, 510, 514, and 516 described above and shown in FIGS. 5, 6, 7, and 8 show the architecture, functionality, and operation of possible implementations of the embodiments of the present invention. In this regard, each block may represent a module, segment, or portion of code, which comprises one or more executable instructions for implementing the specified logical function(s). It should also be noted that in some alternative implementations, the functions noted in the blocks may occur in an order different from that shown in the figures.

It is further emphasized that the above-described embodiments of the present invention, particularly any "preferred" embodiments, are merely possible examples of the implementations that are merely set forth for a clear understanding of the principles of the invention. It will be apparent to those skilled in the art that many modifications and variations may be made to the above-disclosed embodiments of the present invention without departing substantially from the spirit and principles of the invention. All such modifications and variations are intended to be included herein within the scope of the disclosure and present invention and protected by the following claims.

Therefore, having thus described the invention, at least the following is claimed:

1. A filter tuner system, comprising:

a sequential logic configured to provide at least one output signal in response to at least one present input signal and at least one previous input signal;

a register configured to store at least one previous input signal of at least one bit in length as at least one output signal, wherein said register is in electrical communications with said sequential logic;

a comparator configured to compare a plurality of input signals and provide at least one output signal indicative of the comparative condition of said input signals, wherein said comparator is in electrical communications with said register;

a first counter configured to provide at least one output signal comprising a sequence of at least one bit in length, wherein said first counter is in electrical communications with said sequential logic, said register, and said comparator;

a second counter configured to provide at least one output signal comprising a sequence of at least one bit in length, wherein said second counter is in electrical communications with said sequential logic;

a synchronizing logic configured to synchronize a first input of at least one signal with respect to a second input of at least one signal to provide at least one synchronized output signal, wherein said synchronizing logic is in electrical communications with said sequential logic, said first counter, and said second counter;

a first oscillator configured to provide at least one oscillatory output signal, wherein said first oscillator is in electrical communications with said first counter;

a second oscillator configured to provide at least one oscillatory output signal, wherein said second oscillator is in electrical communications with said synchronizing logic and said second counter; and a control logic configured to transmit control signals an received informational signals, wherein said control logic is in electrical communications with said sequential logic, said second oscillator, and said second counter.

2. The system of claim 1, wherein said sequential logic is a finite state machine.

3. The system of claim 1, wherein said synchronizing logic is a synchronizer.

4. The system of claim 1, wherein said first oscillator is a crystal oscillator.

5. The system of claim 1, wherein said second oscillator is comprised of at least one resistance element and at least one capacitance element.

6. The system of claim 1, further comprising:
a first combinational logic configured to provide at least one output signal in response to at least one present first combinational logic input signal, wherein said first combinational logic is in electrical communications with said second counter and said control logic.

7. The system of claim 6, wherein said first combinational logic is further configured to determine at least one of an overflow condition of said second counter and an underflow condition of said second counter.

8. The system of claim 6, further comprising:
a second combinational logic configured to provide at least one output signal in response to at least one present second combinational logic input signal, wherein said second combinational logic is in electrical communications with an external source of oscillating signals, said second oscillator, said synchronizing logic, said second counter, and said control logic.

9. The system of claim 8, wherein said second combinational logic is further configured to selectively output at least one present second combinational logic input signal responsive to at least one control signal transmitted from said control logic.

10. A method for a filter tuner, comprising the steps of executing a calibration cycle comprising the steps of:
resetting a first counter;
resetting a second counter;
starting said first counter to count at a frequency provided by a first oscillator;
starting said second counter to count at a frequency provided by a second oscillator;
stopping said first counter when said second counter reaches a first predetermined count;
stopping said second counter when said second counter reaches a first predetermined count;
storing the count of said first counter in a register;
executing a measurement cycle, comprising the steps of:
resetting said first counter;
resetting said second counter;
starting said first counter to count at a frequency provided by a first oscillator;
starting said second counter to count at a frequency provided by a second oscillator;
stopping said first counter when said first counter reaches a second predetermined count;
stopping said second counter when said first counter reaches a second predetermined count; and
executing a filter tuning cycle, comprising the steps of;
determining a frequency cutoff variation of said filter; and
tuning said filter dependent on said frequency cutoff variation of said filter.

11. The method of claim 10, wherein:
said steps of starting said first counter and starting said second counter, within said step of executing said calibration cycle, occur simultaneously;
said steps of stopping said first counter and stopping said second counter, within said step of executing said calibration cycle, occur simultaneously;
said steps of starting said first counter and starting said second counter, within said step of executing said measurement cycle, occur simultaneously; and
said steps of stopping said first counter and stopping said second counter, within said step of executing said measurement cycle, occur simultaneously.

12. The method of claim 10, wherein said second predetermined count is equivalent to said count stored in said register during said step of storing said count of said first counter in said register.

13. The method of claim 10, wherein:
said step of determining said frequency cutoff comprises determining a difference between said count of said second counter, at said step of stopping said second counter when said first counter reaches a second predetermined count, and said first predetermined count; and
said step of tuning said filter comprises:
mapping said difference to at least one control variable; and
adjusting at least one component of said filter dependent on said control variables.

14. A filter tuner system, comprising:
a sequential logic means for providing at least one output signal in response to at least one present input signal and at least one previous input signal;
a register means for storing at least one previous input signal of at least one bit in length as at least one output signal, wherein said register means is in electrical communications with said sequential logic means;
a comparator means for comparing a plurality of input signals and providing at least one output signal indicative of the comparative condition of said input signals, wherein said comparator means is in electrical communications with said register means;
a first counter means for providing at least one output signal comprising a sequence of at least one bit in length, wherein said first counter means is in electrical communications with said sequential logic means, said register means, and said comparator means;
a second counter means for providing at least one output signal comprising a sequence of at least one bit in length, wherein said second counter means is in electrical communications with said sequential logic means;
a synchronizing logic means for synchronizing a first input of at least one signal with respect to a second input of at least one signal to provide at least one synchronized output signal, wherein said synchronizing logic means is in electrical communications with said sequential logic means, said first counter means, and said second counter means;
a first oscillator means for providing at least one oscillatory output signals, wherein said first oscillator means is in electrical communications with said first counter means;
a second oscillator means configured to provide at least one oscillatory output signals, wherein said second oscillator means is in electrical communications with said synchronizing logic means and said second counter means; and a control logic means configured to transmit control signals and receive informational signals, wherein said control logic means is in electrical communications with said sequential logic means, said second oscillator means, and said second counter means.

15. The system of claim 14, further comprising:

a first combinational logic means for providing at least one output signal in response to at least one present first combinational logic means input signal, wherein said first combinational logic means is in electrical communications with said second counter means and said control logic means.

16. The system of claim 15, wherein said first combinational logic means further provides for determining one of at least an overflow condition of said second counter means and an underflow condition of said second counter means.

17. The system of claim 15, further comprising:

a second combinational logic means for providing at least one output signal in response to at least one present second combinational logic means input signal, wherein said second combinational logic means is in electrical communications with an external source of oscillating signals, said second oscillator means, said synchronizing logic means, said second counter means, and said control logic means.

18. The system of claim 17, wherein said second combinational logic means further provides for selectively outputting at least one present second combinational logic input signal responsive to at least one control signal transmitted from said control logic means.

19. A filter tuner system, comprising:

a filter tuner hardware configured to maintain the cutoff frequency accuracy of a filter; and a control logic in electrical communications with said filter tuner hardware and configured to transmit control signals and receive informational signals;

wherein said filter tuner hardware is further configured to measure the cutoff frequency at the output of said filter using counting logic and to cause the adjustment of a least one component of said filter.

20. The system of claim 19, wherein said control logic comprises at least one of a microprocessor, a programmable logic controller, a hard-wired logic, and a firmware stored in a memory.

21. A method for a filter tuner, comprising the steps of:

calibrating a filter tuner hardware;

measuring the cutoff frequency accuracy of a filter with said filter tuner hardware; and adjusting at least one component of said filter with said filter tuner hardware in order to maintain the cutoff frequency accuracy of said filter.

wherein the filter tuner hardware includes counting logic to measure the cutoff frequency accuracy.

22. The method of claim 21, further comprising the step of tuning a filter to a nominally optimal setting.

* * * * *